(12) United States Patent
Shimada et al.

(10) Patent No.: US 6,676,647 B2
(45) Date of Patent: Jan. 13, 2004

(54) DISPOSABLE PULL-ON UNDERGARMENT

(75) Inventors: Takaaki Shimada, Kagawa-ken (JP); Seiji Suzuki, Kagawa-ken (JP); Nariaki Shimoe, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 190 days.

(21) Appl. No.: 09/864,623

(22) Filed: May 24, 2001

(65) Prior Publication Data

US 2001/0049516 A1 Dec. 6, 2001

(30) Foreign Application Priority Data

May 26, 2000 (JP) .......................... 2000-157024

(51) Int. Cl.[7] .............................. A61F 13/20; A41B 9/00
(52) U.S. Cl. ............................. 604/385.11; 604/385.27; 2/400
(58) Field of Search ....................... 604/385.11, 385.27; 2/400

(56) References Cited

U.S. PATENT DOCUMENTS

| | | | | |
|---|---|---|---|---|
| 5,163,932 A | * | 11/1992 | Nomura et al. ................. 2/401 |
| 5,624,420 A | * | 4/1997 | Bridges et al. ............. 156/290 |
| 5,628,738 A | * | 5/1997 | Suekane .................. 156/308.4 |
| 5,746,731 A | * | 5/1998 | Hisada ...................... 450/154 |
| 5,817,087 A | * | 10/1998 | Takabayashi et al. .. 604/385.29 |
| 6,113,717 A | * | 9/2000 | Vogt et al. ................. 156/73.1 |
| 6,454,752 B1 | * | 9/2002 | Huang et al. ............... 604/389 |
| 6,458,116 B1 | * | 10/2002 | Matsushita .................. 604/396 |
| 2002/0007172 A1 | * | 1/2002 | Takei et al. |

FOREIGN PATENT DOCUMENTS

JP          9-38134          2/1997

* cited by examiner

*Primary Examiner*—William C. Doerrler
*Assistant Examiner*—Filip Zec
(74) *Attorney, Agent, or Firm*—Butzel Long

(57) ABSTRACT

The disposable pull-on undergarment that has first and second waist regions and a crotch region extending between these two waist regions. The waist regions are connected with each other in bonding zones extending along transversely opposite side edge portions thereof so as to define a waist-opening and a pair of leg-openings. First elastic members are bonded under tension to peripheral edge of the waist-opening and second elastic members are bonded under tension to peripheral edges of the leg-openings so that respective opposite ends of the first elastic members are positioned and fixed at first zones defined immediately inside the bonding zones in a circumferential direction of the waist-opening and respective opposite ends of the second elastic members are positioned and fixed at second zones defined immediately inside the bonding zones in a circumferential direction Y of the leg-openings.

3 Claims, 6 Drawing Sheets

DISPOSABLE PULL-ON UNDERGARMENT

BACKGROUND OF THE INVENTION

This invention relates to a disposable pull-on undergarment and more particularly to undergarment such as a disposable pull-on diaper, training pants or incontinent pants.

Japanese Patent Application Publication No. 1997-38134A describes a disposable pull-on undergarment comprising a liquid-pervious topsheet, a liquid-impervious backsheet and a liquid-absorbent core disposed between these two sheets so as to configure front and rear waist regions and a crotch region extending between these two waist regions wherein the waist regions are connected with each other in bonding zones extending along transversely opposite side edge portions of the respective waist regions and thereby a waist-opening and a pair of leg-openings are defined. In each of the bonding zones, a plurality of welding lines are intermittently arranged to be spaced one from another by a predetermined distance longitudinally of the undergarment.

To take off the used undergarment, the front and rear waist regions may be pulled in opposite directions to tear off the undergarment along the bonding zones from the waist-opening toward the leg-openings.

The undergarment is provided with circumferentially stretchable first elastic members bonded under tension to peripheral edge of the waist-opening and with circumferentially stretchable second elastic members bonded under tension to respective peripheral edges of the leg-openings. Circumferentially stretchable third elastic members are bonded under tension to the front and rear waist regions so as to extend across these waist regions.

Each of these elastic members has longitudinally opposite end portions and an intermediate portion. In the case of the first and second elastic members, the opposite end portions and intermediate portion are disposed between the top- and backsheets and intermittently bonded to inner surface of at least one of these sheets by means of adhesive. In the case of the third elastic members, the respective opposite end portions are disposed between the top- and backsheets and intermittently bonded to inner surface of at least one of these sheets by means of adhesive while the intermediate portion is intermittently bonded to inner surface of the backsheet by means of adhesive. The respective opposite end portions of these elastic members partially lie in the bonding zones. The intermediate portion of the third elastic members circumferentially extend across the core.

In the undergarment disclosed in the Publication, the opposite end portions of the first~third elastic members partially lie in the bonding zones and may prevent the used undergarment from being smoothly torn off along the bonding zones.

SUMMARY OF THE INVENTION

It is an object of this invention to provide the disposable pull-on undergarment designed to be smoothly torn off along the bonding zones.

According to this invention, there is provided a disposable pull-on undergarment having first and second waist regions opposed to each other and a crotch region extending between these two waist regions wherein these first and second waist regions are connected with each other in bonding zones extending along transversely opposite side edge portions thereof so as to define a waist-opening and a pair of leg-openings and wherein first elastic members being stretchable circumferentially of the waist regions are bonded under tension to peripheral edge of the waist-opening and second elastic members being stretchable circumferentially of the legs are bonded under tension to peripheral edges of the leg-openings.

According to this invention the first elastic members respectively have first opposite ends and first intermediate portions extending between the first opposite ends, respectively, and the first opposite ends are positioned and fixed at first zones defined immediately inside the bonding zones in a circumferential direction of the waist-opening.

According to one embodiment of this invention, the second elastic members respectively have second opposite ends and second intermediate portions extending between the second opposite ends, respectively, and the second opposite ends are positioned and fixed at second zones defined immediately inside the bonding zones in respective circumferential directions of the leg-openings.

According to another embodiment of this invention, at least one third elastic member lying below the first elastic members and being stretchable in the circumferential direction of the waist-opening is attached under tension to at least one of the first and second waist regions between the peripheral edge of the waist-opening and the peripheral edges of the leg-openings and wherein the third elastic member has third opposite ends and third intermediate portions extending between the third opposite ends and the third opposite ends are positioned and fixed at third zones defined immediately inside the bonding zones in the circumferential direction of the waist-opening.

According to still another embodiment of this invention, a peel strength between the first and second waist regions in the bonding zones is in a range of 4~40 N with respect to 25 mm, a longitudinal dimension of the bonding zone.

DETAILED DESCRIPTION OF THE PREFERRED EMBODIMENTS

Details of a disposable pull-on undergarment according to this invention will be more fully understood from the description of a disposable pull-on diaper as one embodiment given hereunder with reference to the accompanying drawings.

Figure 1:
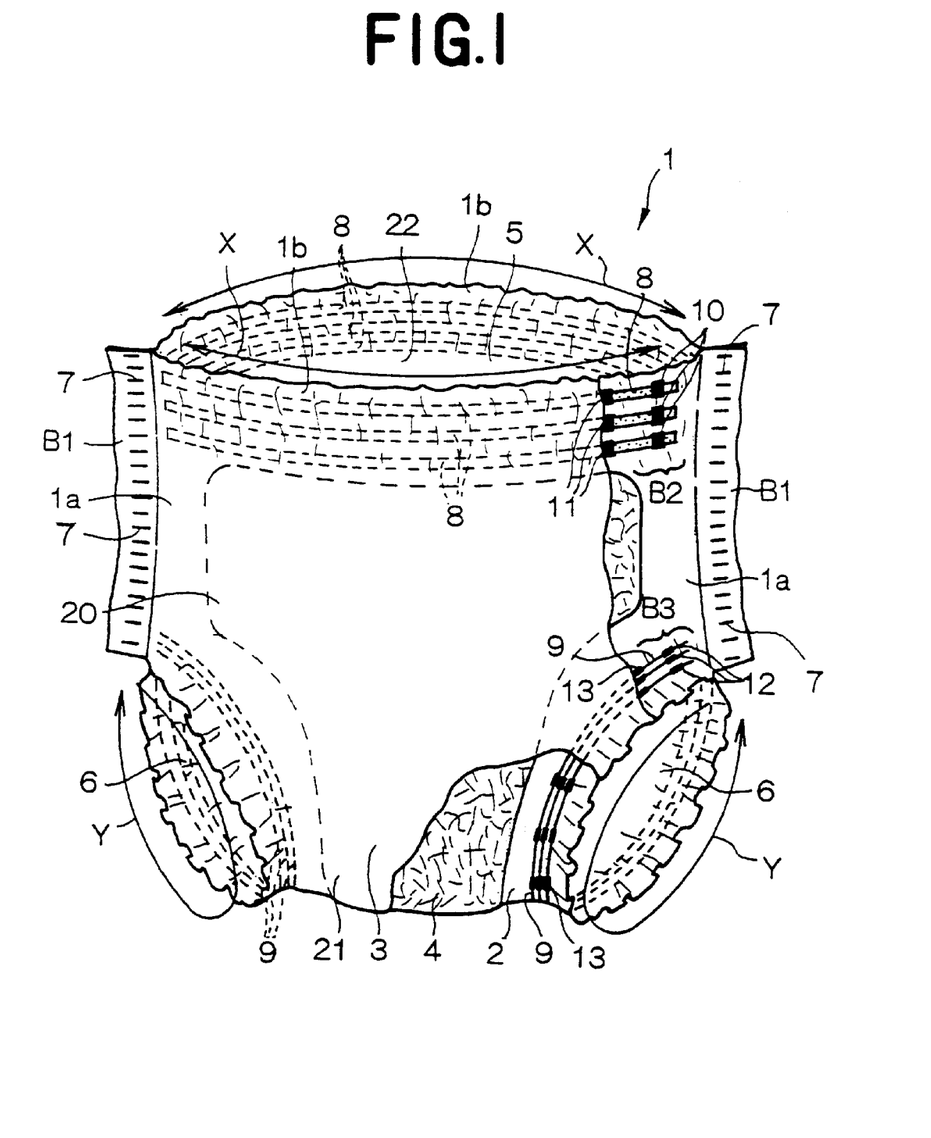
FIG. 1 is a perspective view showing a disposable diaper as a typical embodiment of this invention as viewed from the side a front waist region and partially broken away.
Figure 2:
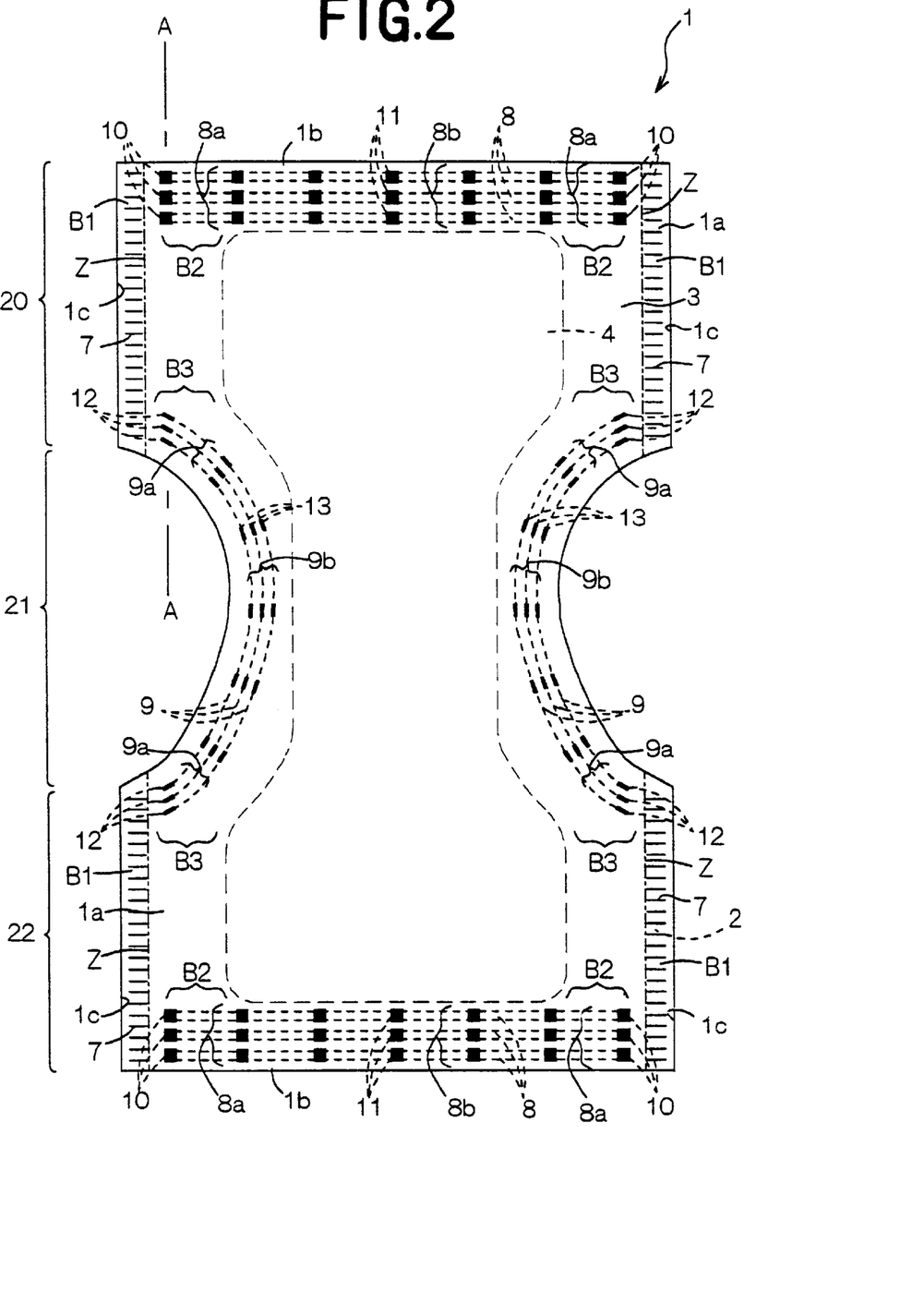
FIG. 2 is an exploded plan view showing the diaper of FIG. 1 as viewed from the side of a backsheet.
Figure 3:
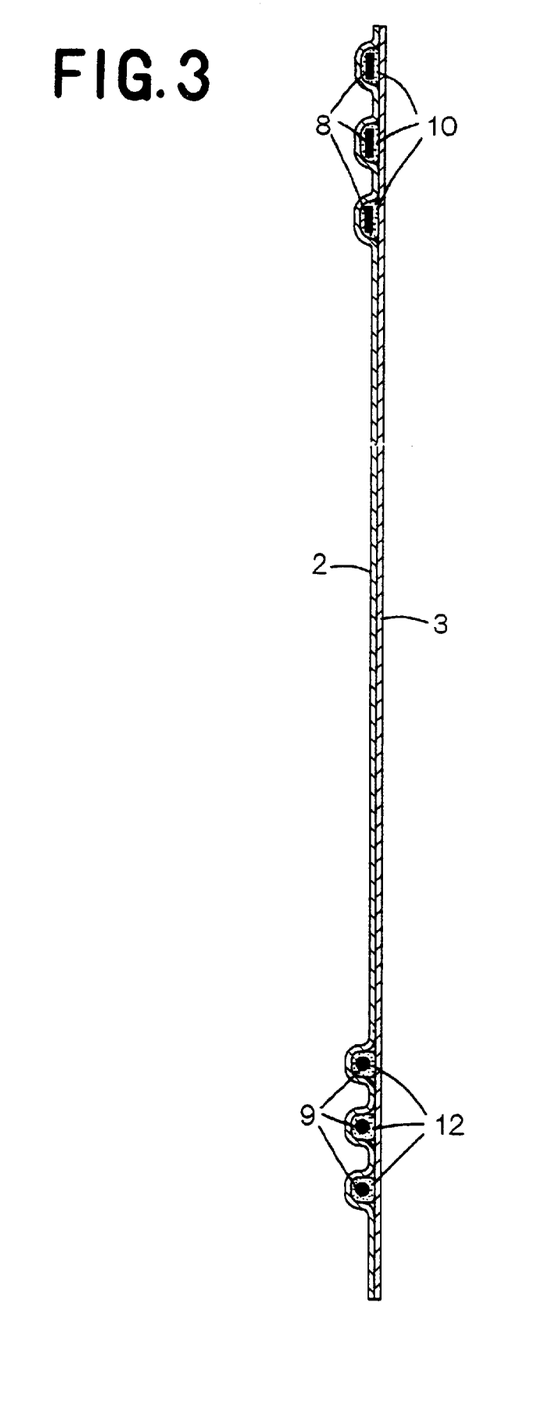
FIG. 3 is a sectional view taken along line A—A in FIG. 2.

FIG. 1 is a perspective view showing a disposable diaper 1 as viewed from the side of a front waist region 20 and partially broken away, FIG. 2 is an exploded plan view of the diaper 1 shown by FIG. 1 as viewed from the side of a backsheet 3 and FIG. 3 is a sectional view taken along line A—A in FIG. 2.

The diaper 1 basically comprises a liquid-pervious topsheet 2, a liquid-impervious backsheet 3 and a liquid-absorbent core 4 disposed between the top- and backsheets 2, 3. The liquid-absorbent core 4 has its entire surface covered with and bonded to liquid-pervious tissue paper (not shown) and the core 4 is bonded to inner surface of at least one of the top- and backsheets 2, 3 via the tissue paper.

As seen in FIG. 2, the diaper 1 has a front waist region 20 (first waist region), a rear waist region 22 (second waist region) and a crotch region 21 extending between the front and rear waist regions 20, 22. The diaper 1 is contoured by transversely opposite side edge portions 1a curving transversely inward to describe circular arcs and longitudinally opposite edge portions 1b extending parallel transversely of the diaper 1. Portions of the top- and backsheets 2, 3 extending outward beyond peripheral edge of the core 4 are placed upon and bonded to each other. Bonding zones B1 extend along the respective transversely opposite side edge portions 1a of the top- and backsheets 2, 3. Each of the bonding zones B1 comprises a plurality of welding lines 7 intermittently arranged so as to be spaced one from another by a predetermined distance longitudinally of the diaper 1. Of the diaper 1, the bonding zones B1 are illustrated to be defined between imaginary lines Z and the adjacent side edges 1c of the front and rear waist regions 20, 22 and to contain therebetween the welding lines 7.

The respective side edge portions 1a of the front and rear waist regions 20, 22 put flat together are bonded together in the respective bonding zones B1 to define a waist-opening 5 opening upward as viewed in FIG. 1 and a pair of leg-openings 6 opening right- and leftward, respectively, as viewed in FIG. 1.

A plurality of elastically stretchable elements 8 (first elastic member) circumferentially extending in a direction X are bonded under tension to peripheral edge of the waist-opening 5. Similarly, a plurality of elastically stretchable elements 9 (second elastic member) circumferentially extending in a direction Y are bonded under tension to respective peripheral edges of the leg-openings 6.

The elastic members 8 associated with the waist-opening have their longitudinally opposite ends 8a (first opposite ends) lying in the transversely opposite side edge portions 1a of the front and rear waist regions 20,22 and an intermediate portions 8b (first intermediate portion) extending between the respective opposite ends 8a. The respective opposite ends 8a are positioned in zones B2 defined immediately inside the respective bonding zones B1 in the circumferential direction X. The elastic members 8 are disposed between the top- and backsheets 2, 3 with their respective opposite ends 8a partially fixed to inner surfaces of these sheets 2, 3 in the respective zones B2 by means of adhesive 10 and with their intermediate portions 8b intermittently fixed to inner surfaces of these sheets 2, 3 by means of adhesive 11.

The elastic members 9 associated with each of the leg-openings have longitudinally opposite ends 9a (second opposite ends) lying in the transversely opposite side edge portions 1a of the front and rear waist regions 20, 22, respectively, and intermediate portions 9b (second intermediate portion) extending between the opposite ends 9a. The opposite ends 9a are positioned in zones B3 defined immediately inside the respective bonding zones B1 in the circumferential direction Y The elastic members 9 are disposed between the top- and backsheets 2, 3 with their respective opposite ends 9a partially fixed to inner surfaces of these sheets 2, 3 in the respective zones B3 by means of adhesive 12 and with their intermediate portions 9b intermittently fixed to the inner surfaces of these sheets 2, 3 by means of adhesive 13.

In the presence of these elastic members 8, 9 incorporated in the diaper 1, the peripheral edge of the waist-opening 5 has a stretchability in its circumferential direction X and the peripheral edges of the leg-openings 6 have a stretchability in their circumferential direction Y. Referring to FIG. 1, a plurality of gathers are formed along the respective peripheral edges of the waist-opening 5 and the leg-openings 6 as the elastic members 8, 9 contract.

Preferably, the respective opposite ends 8a, 9a of the elastic members 8, 9 are firmly fixed to the inner surfaces of the top- and backsheets 2, 3 in order to prevent these opposite ends 8a, 9a from being unintentionally peeled off from the top- and backsheets 3 during use of the diaper 1.

To take the diaper 1 from a wearer's body, the diaper 1 may be torn off along the bonding zones B1 from the waist-opening 5 toward the leg-openings 6. The respective opposite ends 8a, 9a of the elastic members 8, 9 are not present in the bonding zones B1 and therefore only a peel strength of the bonding zones B1 in the welded lines 7 resist operation of tearing off the diaper 1 along the bonding zones B1.

The peel strength of the diaper 1 in the bonding zones B1 is in a range of 4~40 N with respect to 25 mm, a longitudinal dimension of the bonding zone B1. The peel strength less than 4 N/25 mm might unintentionally separate the front and rear waist regions along the bonding zones B1 as a tensile force tending to enlarge the peripheral edge of the waist-opening and the peripheral edges of the leg-openings is exerted on the diaper 1. The peel strength exceeding 40 N/25 mm might require a remarkable force to tear off the diaper 1 along the bonding zones B1.

Figure 4:
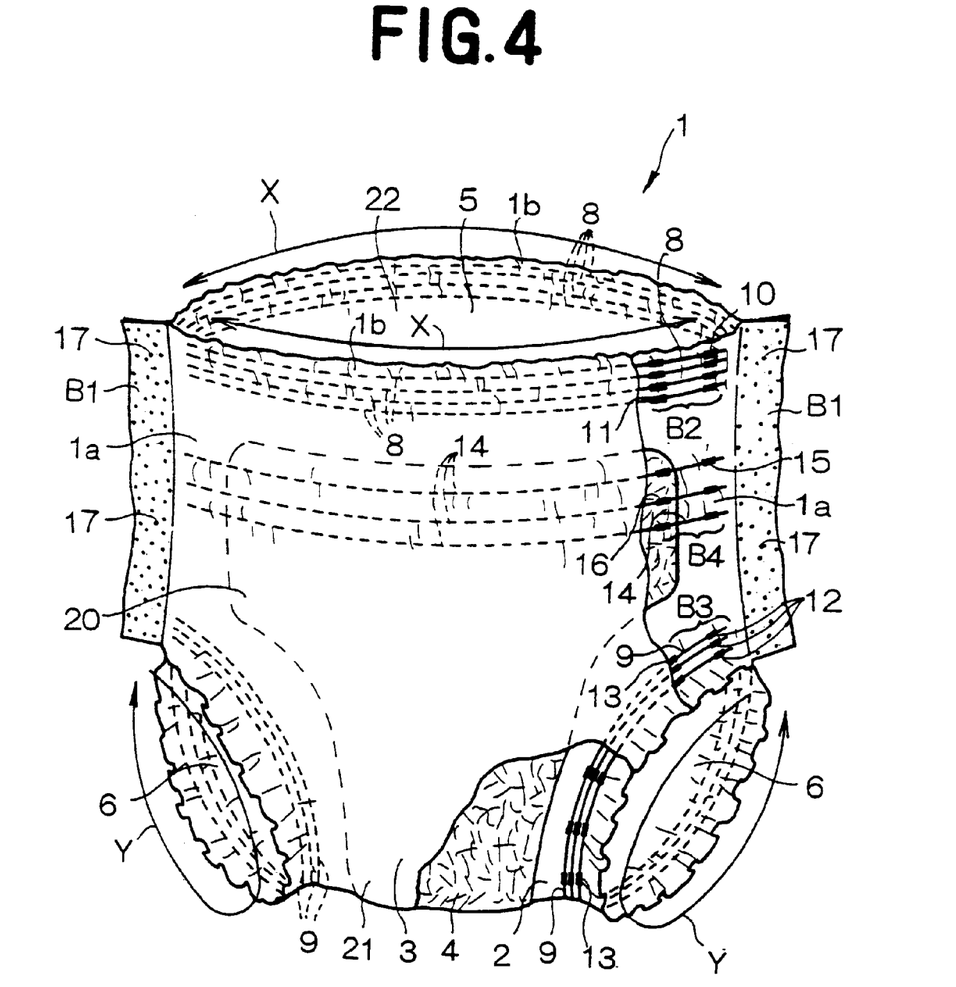
FIG. 4 is a perspective view showing another embodiment of the diaper according to the invention as viewed from the side of the front waist region and partially broken away.
Figure 5:
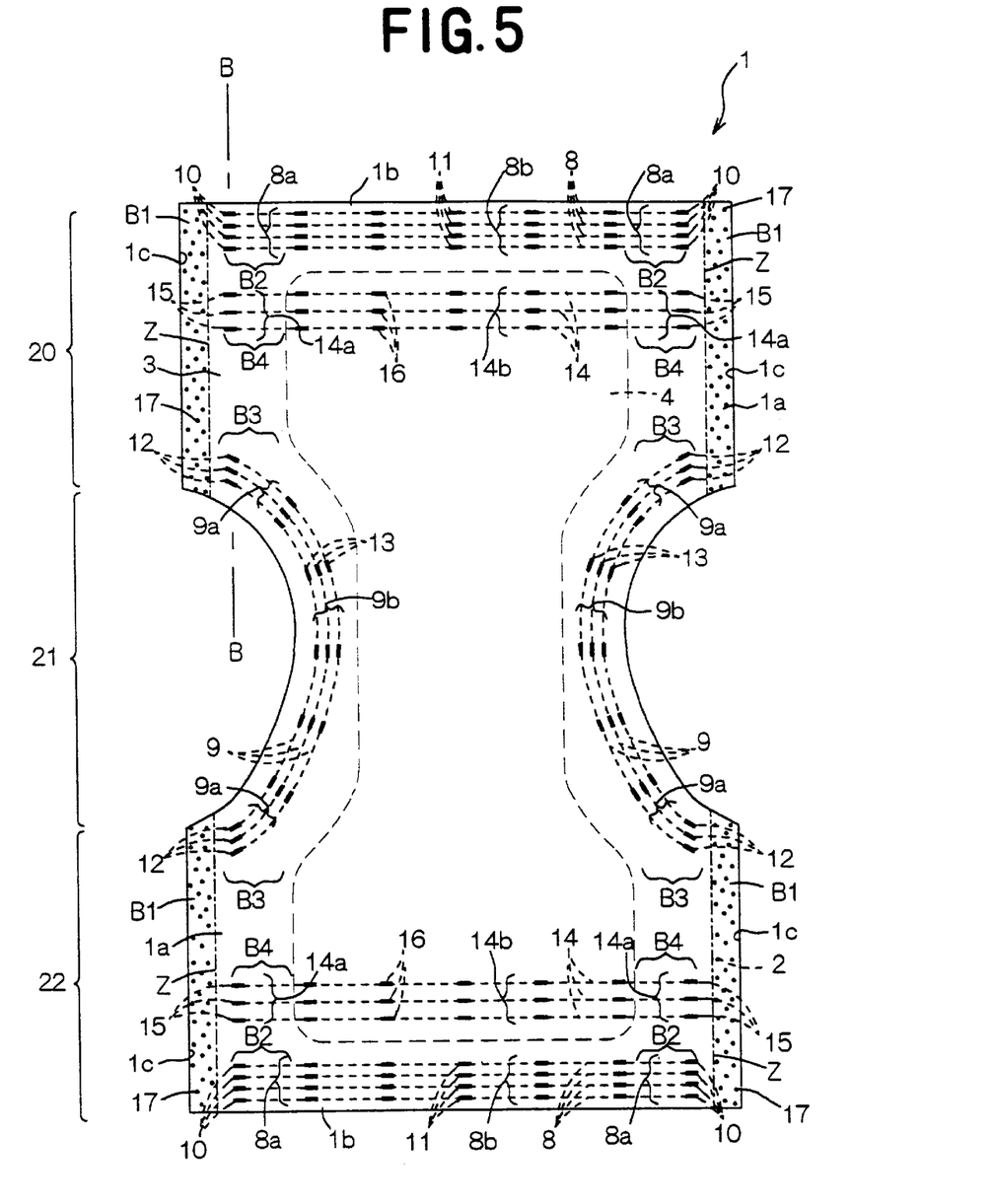
FIG. 5 is an exploded plan view showing the diaper of FIG. 4 as viewed from the side of the backsheet.
Figure 6:
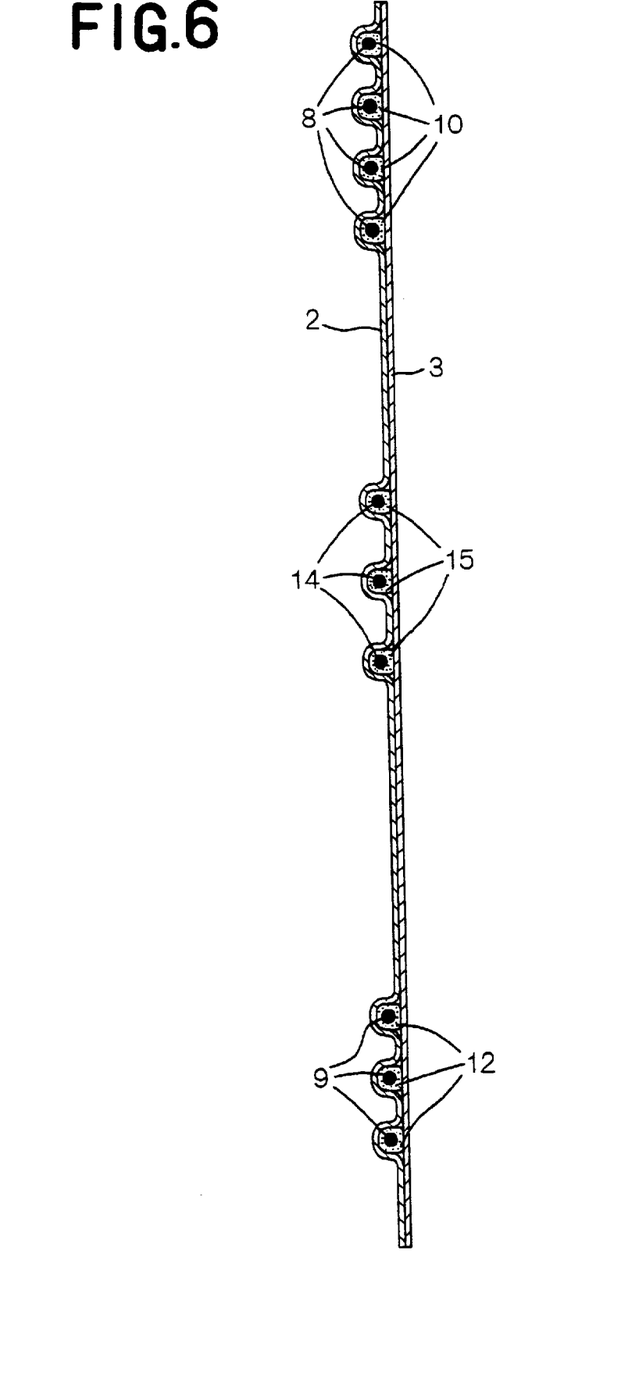
FIG. 6 is a sectional view taken along line B—B in FIG. 5.

FIG. 4 is a perspective view showing another embodiment of the diaper 1 as viewed from the side of the front waist region 20 and partially broken away, FIG. 5 is an exploded plan view showing the diaper 1 of FIG. 4 as viewed from the side of the rear waist region and FIG. 6 is a sectional view taken along line B—B in FIG. 5.

The diaper 1 comprises a liquid-pervious topsheet 2, a liquid-impervious backsheet 3 and a liquid-absorbent core 4 having its entire surface being covered with and bonded to water-pervious tissue paper (not shown). These sheets 2, 3 and core 4 configure together a front waist region 20 (first waist region), a rear waist region 22 (second waist region) and a crotch region 21 extending between the front and rear waist regions 20, 22. The diaper 1 is contoured by transversely opposite side edge portions 1a longitudinally extending partially parallel to each other and partially curved inward transversely of the diaper 1 to describe circular arcs and longitudinally opposite edge portions 1b transversely extending parallel to each other.

The transversely opposite side edge portions 1a of the front and rear waist regions 20, 22 put flat together are bonded together in the bonding zones B1 to define a waist-opening 5 opening upward as viewed in FIG. 4 and a pair of leg-openings 6 opening right- and leftward as viewed in FIG. 4.

The diaper 1 FIG. 4 is distinguished from the diaper 1 of FIG. 1 in that the adhesive 17 is applied in the form of dots as will be best seen in FIG. 5. In this diaper 1, the bonding zones B1 are defined between imaginary lines Z and the adjacent side edges 1c of the front and rear waist regions 20, 22 and these bonding zones B1 are coated with the dot-like adhesive 17.

The front and rear waist regions 20, 22 of the diaper 1 are provided with, in addition to the elastic members 8 associated with the waist-opening (first elastic members) and the elastic members 9 associated under the leg-openings, a plurality of auxiliary elastic members 14 (third elastic members) that are positioned and fixed under tension to the diaper 1 below the elastic members associated with the waist-opening so as to extend in its circumferential direction X. The auxiliary elastic members 14 are attached to the front and rear waist regions 20, 22 and extend across the core 4 in the circumferential direction X of the waist-opening.

The auxiliary elastic members 14 respectively have opposite ends 14a (third opposite ends) lying on the respective opposite side edge portions 1a and intermediate portions 14b (third intermediate portions) extending between the respective opposite ends 14a. The respective opposite ends 14a are positioned in zones (B4) (third zones) defined immediately inside the respective bonding zones B1 in the circumferential direction of the waist-opening. The respective opposite ends 14a of the auxiliary elastic members 14 are disposed between the top- and backsheets 2, 3 and partially fixed to the inner surfaces of these sheets 2, 3 by means of adhesive 15. The respective intermediate portions 14b are disposed between the backsheet 3 and the core 4 and intermittently fixed to the inner surface at least of the backsheet 3 by means of adhesive 16.

In the presence of these elastic members 8, 9, 14 incorporated in the diaper 1, the peripheral edge of the waist-opening 5 has a stretchability in its circumferential direction X and the peripheral edges of the leg-openings 6 have a stretchability in their circumferential direction Y. Referring to FIG. 4, a plurality of gathers are formed with the respective peripheral edges of the waist-opening 5 and the leg-openings 6 as the elastic members 8, 9, 14 contract.

The auxiliary elastic member 14 attached to the front waist region 20 cooperates with the elastic members 8 associated with the waist-opening to ensure a desired fitness of the diaper 1 around the wearer's waist region and, at the same time, to place the core 4 against the wearer's skin. The auxiliary elastic member 14 may be attached to one or both of the front and rear waist regions 20, 22.

To eliminate an anxiety that the opposite ends 8a, 9a, 14a of the respective elastic members 8, 9, 14 might be peeled off from the top- and backsheets 2, 3, these opposite ends 8a, 9a, 14a should be firmly bonded to the respective inner surfaces of the top- and backsheets 2, 3.

The opposite ends 8a, 9a, 14a of the respective elastic members 8, 9, 14 are absent in the bonding zones B1 and therefore a factor which will resist tearing off of the diaper 1 along the bonding zones B1 is only a peel strength of the adhesive in these bonding zones B1. The diaper 1 shown by FIG. 4 is similar to the diaper 1 shown by FIG. 1 in that the peel strength in the bonding zone B1 is in a range of 4~40 N/25 mm of the bonding zone B1 as measured longitudinally thereof.

The topsheet 2 may be formed with a liquid-pervious sheet such as a nonwoven fabric or a porous plastic film, more preferably with a liquid-pervious and hydrophilic sheet. The backsheet 3 may be formed with a hydrophobic nonwoven fabric, a liquid-impervious plastic film or a laminated sheet consisting of a hydrophobic nonwoven fabric and a plastic film, more preferably with a breathable and liquid-impervious sheet. It is also possible to form the backsheet 3 with a composite nonwoven fabric (SMS nonwoven fabric) comprising a highly water-resistant and flexible melt blown nonwoven fabric and two layers of spun bond nonwoven fabric sandwiching therebetween the opposite sheet surfaces of the melt blown nonwoven fabric.

The nonwoven fabric used for this invention may be of various types such as spun lace-, needle punch-, melt blown-, thermal bond-, spun bond- and chemical bond-types. The component fiber may be selected from a group including polyolefine-based fiber, polyester-based fiber, polyamide-based fiber and thick-and-thin type or side-by-side type conjugated fiber of polyethylene/polypropylene or polyester.

The elastic members 8, 9, 14 may be formed with thread-, filament-, film- or ribbon-like elastomer of natural or synthetic rubber. The elastic members 8 associated with the waist-opening and the elastic members 9 associated with the respective leg-openings in the diaper 1 illustrated by FIGS. 1 and 4 may be alternatively arranged. According to this alternative embodiment, the respective opposite ends 8a, 9a of these elastic members 8, 9 may be continuously fixed to the inner surfaces of the top- and backsheets 2, 3 by means of adhesive 10, 12, respectively, in the zones B2, B3 and the intermediate portions 8b, 9b of these elastic members 8, 9 may be also continuously fixed to the inner surfaces of the top- and backsheets 2, 3 by means of adhesive 11, 13, respectively. The auxiliary elastic members 14 in the diaper 1 illustrated by FIG. 4 may be also alternatively arranged. According to this alternative embodiment, the respective opposite ends 14a of the auxiliary elastic members 14 may be continuously fixed to the inner surfaces of the top- and backsheets 2, 3 in the zones B4 by means of adhesive 15 and their intermediate portions 14b may be continuously fixed to the inner surfaces of the backsheet 3 and the core 4, at least of the backsheet 3 by means of adhesive 16.

The core 4 comprises a mixture of fluff pulp obtained by crushing wood pulp and high absorption polymer grains compressed to a desired thickness. The high absorption polymer may be selected from a group including graft polymer of starch, modified cellulose, crosslinked water-soluble polymer and self-crosslinked alkali metal acrylate.

Bonding the sheets 2, 3 to each other or to the core 4 may be carried out by means of suitable adhesive such as hot melt adhesive or pressure-sensitive adhesive, or using suitable welding technique such as heat sealing or supersonic sealing technique. Hot melt adhesive is particularly preferable as the adhesive means 10, 11, 12, 13, 15, 16, 17. In addition to adhesive means 10, 11, 12, 13, 15, 16, 17, the technique of welding may be also used for the purpose of fixation of the elastic members 8, 9, 14.

This invention is not limited to a disposable diaper but applicable also to the other disposable pull-on undergarment such as training pants or incontinent pants.

In the disposable pull-on undergarment according to this invention, the respective opposite ends of the elastic members are positioned and fixed in the zones defined immediately inside the bonding zones in the circumferential directions of the waist- and leg-openings, respectively. Such unique arrangement enables the used wearing article to be smoothly torn off along the bonding zones without being resisted by the respective opposite ends of the elastic members.

Furthermore, the disposable pull-on undergarment according to this invention has a peel strength along the bonding zones adjusted to 4~40 N with respect to 25 mm, a longitudinal dimension of the bonding zone. With an advantageous consequence, it is not apprehended that the disposable pull-on undergarment might be unintentionally peeled off along the bonding zones, on one hand, and no troublesome effort is necessary to tear off the used pull-on undergarment along the bonding zones, on the other hand.

What is claimed is:

1. A disposable pull-on undergarment comprising:

front and rear waist regions opposed to each other;

a crotch region extending between said front and rear waist regions;

bonding zones connecting said front and rear waist regions to one another, and extending along transversely opposite side edge portions of said front and rear waist regions so as to define a waist-opening having a circumference and a pair of leg-openings each having a circumference;

first elastic members bonded under tension to a peripheral edge of the waist-opening and being stretchable circumferentially of said first and second waist regions;

second elastic members bonded under tension to peripheral edges of the leg-openings and being stretchable circumferentially of said leg-openings; and at least one third elastic member laying below said first elastic members and being stretchable in said circumferential direction of said waist-opening, said first elastic members extending substantially along the entire circumference of the waist-opening exclusive of bonding zones, said at least one third elastic member being attached under tension to at least one of said front arid rear waist regions between the peripheral edge of said waist-opening and said peripheral edges of said leg-openings, each of said at least one third elastic members extending substantially along the entire circumference of the waist-opening exclusive of bonding zones.

2. The disposable pull-on undergarment according to claim 1, wherein said second elastic members extend substantially along the entire circumference of the leg-openings exclusive of bonding zones.

3. The disposable pull-on undergarment according to claim 1, wherein a peel strength between the front and rear waist regions in said bonding zones is in a range of about 4 to about 40 N with respect to a 25 mm longitudinal dimension of said bonding zone.

* * * * *

(12) EX PARTE REEXAMINATION CERTIFICATE (5915th)
United States Patent
Shimada et al.

(10) Number: US 6,676,647 C1
(45) Certificate Issued: Oct. 2, 2007

(54) DISPOSABLE PULL-ON UNDERGARMENT (75) Inventors: Takaaki Shimada, Kagawa-ken (JP); Seiji Suzuki, Kagawa-ken (JP); Nariaki Shimoe, Kagawa-ken (JP)

(73) Assignee: Uni-Charm Corporation, Kinsei-Cho Kawanoe-Shi, Ehime-Ken (JP)

Reexamination Request:
No. 90/007,486, Feb. 23, 2005

Reexamination Certificate for:
Patent No.: 6,676,647
Issued: Jan. 13, 2004
Appl. No.: 09/864,623
Filed: May 24, 2001

(30) Foreign Application Priority Data

May 26, 2000 (JP) ........................................ 2000-157024

(51) Int. Cl.
*A61F 13/20* (2006.01)
*A41B 9/00* (2006.01)

(52) U.S. Cl. .............................. 604/385.11; 604/385.27; 2/400

(58) Field of Classification Search ............. 604/385.11, 604/385.26, 385.27, 385.29
See application file for complete search history.

(56) References Cited

U.S. PATENT DOCUMENTS 4,909,804 A    3/1990  Douglas, Sr.
5,858,012 A *  1/1999  Yamaki et al. .......... 604/385.27
5,876,392 A *  3/1999  Hisada ................... 604/385.29
5,916,206 A *  6/1999  Otsubo et al. ......... 604/385.27
5,941,865 A *  8/1999  Otsubo et al. ......... 604/385.29
6,179,820 B1 * 1/2001  Fernfors ................ 604/385.27

FOREIGN PATENT DOCUMENTS

EP           0873738           10/1998

* cited by examiner

*Primary Examiner*—Jimmy G. Foster (57) ABSTRACT

The disposable pull-on undergarment that has first and second waist regions and a crotch region extending between these two waist regions. The waist regions are connected with each other in bonding zones extending along transversely opposite side edge portions thereof so as to define a waist-opening and a pair of leg-openings. First elastic members are bonded under tension to peripheral edge of the waist-opening and second elastic members are bonded under tension to peripheral edges of the leg-openings so that respective opposite ends of the first elastic members are positioned and fixed at first zones defined immediately inside the bonding zones in a circumferential direction of the waist-opening and respective opposite ends of the second elastic members are positioned and fixed at second zones defined immediately inside the bonding zones in a circumferential direction Y of the leg-openings.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 2 is cancelled.

Claim 1 is determined to be patentable as amended.

Claim 3, dependent on an amended claim, is determined to be patentable.

1. A disposable pull-on undergarment comprising:
   *a topsheet and a backsheet;*
   front and rear waist regions opposed to each other;
   a crotch region extending between said front and rear waist regions;
   bonding zones connecting said front and rear waist regions to one another, and extending along transversely opposite side edge portions of said front and rear waist regions so as to define a waist-opening having a circumference and a pair of leg-openings each having a circumference;
   first elastic members bonded under tension to a peripheral edge of the waist-opening and being stretchable circumferentially of said first and second waist regions;
   second elastic members bonded under tension to peripheral edges of the leg-openings and being stretchable circumferentially of said leg-openings *and extending substantially along the entire circumference of the leg-openings exclusive of bonding zones*; and
   at least one third elastic member laying below said first elastic members and being stretchable in said circumferential direction of said waist-opening,
   said first elastic members extending substantially along the entire circumference of the waist-opening exclusive of bonding zones,
   said at least one third elastic member being attached under tension to at least one of said front and rear waist regions between the peripheral edge of said waist-opening and said peripheral edges of said leg-openings, each of said at least one third elastic members extending substantially along the entire circumference of the waist-opening exclusive of bonding zones,
   *said first elastic members and each of said at least one third elastic members being positioned immediately between the topsheet and the backsheet and bonded to each of the topsheet and backsheet.*

\* \* \* \* \*